(12) United States Patent
Morris

(10) Patent No.: US 8,287,530 B2
(45) Date of Patent: *Oct. 16, 2012

(54) COMPACT ELECTROSURGERY APPARATUS

(75) Inventor: Marcia L. Morris, St. Paul, MN (US)

(73) Assignee: Genii, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/296,811

(22) Filed: Nov. 15, 2011

(65) Prior Publication Data

US 2012/0059369 A1    Mar. 8, 2012

Related U.S. Application Data

(63) Continuation of application No. 11/940,595, filed on Nov. 15, 2007, now Pat. No. 8,083,735.

(60) Provisional application No. 60/866,298, filed on Nov. 17, 2006.

(51) Int. Cl.
*A61B 18/12* (2006.01)

(52) U.S. Cl. ............................ 606/37; 606/34

(58) Field of Classification Search ............... 606/34, 606/37–40

See application file for complete search history.

(56) References Cited

U.S. PATENT DOCUMENTS

| | | | |
|---|---|---|---|
| 4,057,064 A | 11/1977 | Morrison, Jr. et al. |
| 4,060,088 A | 11/1977 | Morrison, Jr. et al. |
| 4,082,993 A | 4/1978 | Oakes |
| 4,171,700 A | 10/1979 | Farin |
| 4,177,828 A | 12/1979 | Vache |
| 4,231,372 A | 11/1980 | Newton |
| 4,244,371 A | 1/1981 | Farin |
| 4,416,276 A | 11/1983 | Newton et al. |
| 4,416,277 A | 11/1983 | Newton et al. |
| 4,658,815 A | 4/1987 | Farin et al. |
| 4,658,819 A | 4/1987 | Harris et al. |
| 4,781,175 A | 11/1988 | McGreevy et al. |
| 4,788,977 A | 12/1988 | Farin et al. |
| 4,799,480 A | 1/1989 | Abraham et al. |
| 4,860,745 A | 8/1989 | Farin et al. |
| 4,890,073 A | 12/1989 | Flachenecker et al. |
| 4,922,210 A | 5/1990 | Flachenecker et al. |
| 4,969,885 A | 11/1990 | Farin |
| 5,062,031 A | 10/1991 | Flachenecker et al. |
| 5,087,257 A | 2/1992 | Farin et al. |

(Continued)

OTHER PUBLICATIONS

Brochure: APC 300 TM, Argon Plasma Coagulation for Open and Endoscopic Applications, ERBE USA Incorporated Surgical Systems, believed dated Feb. 2004 (4 pages).

(Continued)

*Primary Examiner* — Linda Dvorak
*Assistant Examiner* — Samantha Good
(74) *Attorney, Agent, or Firm* — Viksnins Harris & Padys PLLP

(57) ABSTRACT

The invention features compact apparatuses useful in electrosurgery. The compact apparatuses have a housing having a cavity, an electrosurgical system located within the cavity, the electrosurgical system having optionally a monopolar output system, optionally a bipolar output system, optionally an argon plasma coagulation output system, a processor located within the cavity, the processor operatively coupled to each output system of the electrosurgical system to control outputs generated by each output system, optionally a high frequency generator located within the cavity and operatively coupled to the processor; and a gas canister holder and control system located within the cavity of the housing for receiving a gas canister within the cavity of the housing.

17 Claims, 9 Drawing Sheets

U.S. PATENT DOCUMENTS

| | | |
|---|---|---|
| 5,088,997 A | 2/1992 | Delahuerga et al. |
| 5,207,675 A | 5/1993 | Canady |
| 5,217,457 A | 6/1993 | Delahuerga et al. |
| 5,226,904 A | 7/1993 | Gentelia et al. |
| 5,244,462 A | 9/1993 | Delahuerga et al. |
| 5,267,994 A | 12/1993 | Gentelia et al. |
| 5,267,997 A | 12/1993 | Farin et al. |
| 5,300,070 A | 4/1994 | Gentelia et al. |
| 5,330,469 A | 7/1994 | Fleenor |
| 5,372,596 A | 12/1994 | Klicek et al. |
| 5,376,089 A | 12/1994 | Smith |
| 5,484,435 A | 1/1996 | Fleenor et al. |
| 5,496,312 A | 3/1996 | Klicek |
| 5,599,344 A | 2/1997 | Paterson |
| 5,599,348 A | 2/1997 | Gentelia et al. |
| 5,609,573 A | 3/1997 | Sandock |
| 5,626,575 A | 5/1997 | Crenner |
| 5,637,111 A | 6/1997 | Sutcu et al. |
| 5,695,494 A | 12/1997 | Becker |
| 5,720,745 A | 2/1998 | Farin et al. |
| 5,776,092 A | 7/1998 | Farin et al. |
| 5,868,742 A | 2/1999 | Manes et al. |
| 5,921,984 A | 7/1999 | Sutcu et al. |
| 6,063,084 A | 5/2000 | Farin |
| 6,068,627 A | 5/2000 | Orszulak et al. |
| 6,197,026 B1 | 3/2001 | Farin et al. |
| 6,210,410 B1 | 4/2001 | Farin et al. |
| 6,225,593 B1 | 5/2001 | Howieson et al. |
| 6,346,108 B1 | 2/2002 | Fischer |
| 6,391,027 B1 | 5/2002 | Farin et al. |
| 6,419,675 B1 | 7/2002 | Gallo, Sr. |
| 6,475,215 B1 | 11/2002 | Tanrisever |
| 6,511,479 B2 | 1/2003 | Gentelia et al. |
| 6,579,289 B2 | 6/2003 | Schnitzler |
| D477,082 S | 7/2003 | Bromley |
| D477,408 S | 7/2003 | Bromley |
| 6,608,267 B2 | 8/2003 | Fischer et al. |
| 6,830,569 B2 | 12/2004 | Thompson et al. |
| 6,835,082 B2 | 12/2004 | Gonnering |
| 6,875,210 B2 | 4/2005 | Refior et al. |
| 6,939,347 B2 | 9/2005 | Thompson |
| 6,942,660 B2 | 9/2005 | Pantera et al. |
| 6,948,503 B2 | 9/2005 | Refior et al. |
| 7,001,382 B2 | 2/2006 | Gallo, Sr. |
| 7,066,933 B2 | 6/2006 | Hagg |
| 7,122,035 B2 | 10/2006 | Canady |
| 8,083,735 B2 * | 12/2011 | Morris .................. 606/37 |
| 2002/0062131 A1 | 5/2002 | Gallo, Sr. |
| 2002/0133175 A1 | 9/2002 | Carson |
| 2004/0024395 A1 | 2/2004 | Ellman et al. |
| 2004/0147919 A1 | 7/2004 | Behl et al. |
| 2005/0001395 A1 | 1/2005 | Fuentes |
| 2005/0171528 A1 | 8/2005 | Sartor et al. |
| 2005/0240172 A1 | 10/2005 | Hagg et al. |
| 2005/0267456 A1 | 12/2005 | Kuhner |
| 2006/0009763 A1 | 1/2006 | Goble et al. |
| 2006/0036239 A1 | 2/2006 | Canady |
| 2006/0052771 A1 | 3/2006 | Sartor et al. |
| 2006/0052772 A1 | 3/2006 | Sartor et al. |
| 2006/0122586 A1 | 6/2006 | Geiselhart |
| 2006/0178671 A1 | 8/2006 | Canady |
| 2006/0200122 A1 | 9/2006 | Sartor et al. |
| 2006/0229600 A1 | 10/2006 | Canady |

OTHER PUBLICATIONS

Brochure: ERBE ICC 200 E, The Electrosurgical Workstation for Flexible Endoscopy, Multi-Function Electrosurgery for Endoscopy, ERBE USA Incorporated Surgical Systems, believed dated Jan. 2003 (2 pages).

Brochure: UGI-3000B TM, GI Endoscopy Therapy System, Meditron TM, a division of CooperSurgical, Inc., believed dated Jul. 2002 (2 pages).

Brochure: EIP2 ERBE Irrigation Pump, ERBE USA Incorporated Surgical Systems, believed dated Jun. 2005 (2 pages).

Brochure: VIO System, Your System. Your Way., ERBE USA Incorporated Surgical Systems, believed dated Jul. 2004 (5 pages).

http://www.erbe-usa.com/products/vio.asp, posted Oct. 26, 2007 (2 pages).

http://www.erbe-usa.com/products/VIO-300D-Electrosurgical-Generator.asp, posted Oct. 26, 2007 (2 pages).

http://www.erbe-usa.com/products/electrosurgery.asp, posted Oct. 26, 2007 (one page).

VIO 300 D—Electrosurgical Generator. Products [online]. Erbe USA, Nov. 20, 2004 [retrieved from the Internet: <URL:http://web.archive.org/web/20041120112204/http://www.erbe-usa.com-/products/VIO-300D-Electrosurgical-Generator.asp >.

KLS Martin Group, "Electrosurgery", pp. 1-12, May 2006, http://www.ljmedical.dk/SE/Docs/kls_martin/90-288-02-04_05_06_maxium.pdf.

* cited by examiner

COMPACT ELECTROSURGERY APPARATUS

PRIORITY CLAIMED

This application is a continuation of U.S. application Ser. No. 11/940,595, filed on Nov. 15, 2007 (which issued as U.S. Pat. No. 8,083,735 on Dec. 27, 2011), which claims priority to U.S. Ser. No. 60/866,298, filed Nov. 17, 2006, the entirety of which are incorporated herein by reference.

TECHNICAL FIELD

This invention relates to apparatuses useful in electrosurgery.

BACKGROUND

Electrosurgery is surgery performed by electrical methods. Its development has been driven by the clinical need to control bleeding during surgical procedures. While heat has been used medically to control bleeding for thousands of years, the use of electricity to produce heat in tissue has only been in general use since the mid 1920's, and in flexible endoscopy since the 1970's. Electrosurgery offers at least one unique advantage over mechanical cutting and thermal application: the ability to cut and coagulate tissue at the same time. This advantage makes it the ideal surgical tool for the gastroenterologist.

Electrosurgical Generators provide the high frequency electrical energy required to perform electrosurgery and some of these are equipped with an option to use argon gas enchanced electrosurgery. Argon gas enchanced or Argon Plasma Coagulation (APC) has been in long use in the operating room setting and is used intermittently, usually for parenchymal organ surgeries. The apparatus are typically large, heavy and cumbersome systems as shown in FIG. 1. The electrosurgical apparatus has a console system 11 mounted on a cart. Also located on the cart is a large gas canister 13, particularly an argon gas canister, that is coupled to the console to allow a user to perform argon plasma coagulation using the apparatus as is well known. Because the apparatus is so large, heavy and cumbersome, it is difficult to move from one location to another and thus tends to remain near or in one operating room.

About 10 years ago, argon plasma equipped electrosurgery systems were finally adapted to be able to be used in flexible endoscopic procedures of the gut and lung. This required systems with a low flow rate of argon, and long, flexible accessories suitable for these closed procedures. APC is an ideal therapy for the blood rich gut and lung, and its use in flexible endoscopy has increased dramatically. However, when the old operating room argon equipped electrosurgery generators were modified for flexible endoscopy use, little was done to change the overall configuration of the apparatus. This is a disadvantage because flexible endoscopy is often done in multiple room outpatient areas where the lack of mobility of the current units becomes a limiting factor in which and how many, patients are able to receive, and benefit from, APC treatment.

SUMMARY

According to a first aspect of the invention, there is provided a compact electrosurgical apparatus including a housing, an electrosurgical system, a processor, a high frequency generator and a gas canister hold and control system. The housing has a front panel, a back panel generally parallel with the front panel, a top panel extending between the front and back panel, a bottom panel extending between the front and back panel, the bottom panel being generally parallel to the top panel, a left side panel extending between the front, back, top and bottom panels and a right side panel extending between the front, back, top and bottom panels, the right side panel being generally parallel to the left side panel, wherein the front, back, top, bottom left and right side panels define a cavity. The electrosurgical system is located within the cavity includes a monopolar output system, a bipolar output system and an argon plasma coagulation output system. The processor located within the cavity is operatively coupled to each output system of the electrosurgical system to control outputs generated by each output system. The high frequency generator is located within the cavity and is operatively coupled to the processor. The gas canister holder and control system is located within the cavity of the housing for receiving a gas canister within the cavity of the housing.

According to a second aspect of the invention, there is provided a compact electrosurgical apparatus including a housing, an electrosurgical system, a processor and a gas canister hold and control system. The housing has a front panel, a back panel generally parallel with the front panel, a top panel extending between the front and back panel, a bottom panel extending between the front and back panel, the bottom panel being generally parallel to the top panel, a left side panel extending between the front, back, top and bottom panels and a right side panel extending between the front, back, top and bottom panels, the right side panel being generally parallel to the left side panel, wherein the front, back, top, bottom left and right side panels define a cavity. The electrosurgical system is located within the cavity. The processor located within the cavity is operatively coupled to each output system of the electrosurgical system to control outputs generated by each output system. The gas canister holder and control system is located within the cavity of the housing for receiving a gas canister within the cavity of the housing.

According to a third aspect of the invention, there is provided a compact electrosurgical apparatus including a housing, an electrosurgical system, a processor and a gas canister hold and control system. The housing has a front panel, a back panel generally parallel with the front panel, a top panel extending between the front and back panel, a bottom panel extending between the front and back panel, the bottom panel being generally parallel to the top panel, a left side panel extending between the front, back, top and bottom panels and a right side panel extending between the front, back, top and bottom panels, the right side panel being generally parallel to the left side panel, wherein the front, back, top, bottom left and right side panels define a cavity. The electrosurgical system is located within the cavity includes a monopolar output system, a bipolar output system and an argon plasma coagulation output system. The processor located within the cavity is operatively coupled to each output system of the electrosurgical system to control outputs generated by each output system. The gas canister holder and control system is located within the cavity of the housing for receiving a gas canister within the cavity of the housing.

Embodiments of the present invention provide a compact argon plasma capable electrosurgical apparatus for electrosurgery, which is ideal for flexible endoscopy. The compact electrosurgical apparatus contains a processor, a foot pedal system, an electrosurgical system, a lavage pump system, and a high frequency generator; wherein the processor is operably linked to and controls the electrosurgical system, the lavage pump system, and the generator; wherein the electrosurgical system includes a bipolar output system, a monopolar output system, and an argon plasma coagulation (APC) output system; and wherein the processor receives signals from the foot pedal system.

In certain embodiments, the apparatus contains an electrosurgical system, which includes; a high frequency generator; an adjustable bipolar output system including a bipolar mode selector, a bipolar probe socket, and a bipolar wattage indicator; an adjustable monopolar output system including a monopolar mode selector, a monopolar active cord/probe socket, monopolar selectable waveform indicator, a monopolar wattage indicator; an argon plasma coagulation (APC) system including an APC wattage indicator; APC probe socket, an argon gas source connector, argon gas purge control, an argon gas flow rate adjuster, an argon gas flow rate indicator, an APC mode selector, and an argon gas canister volume indicator; a ground pad (neutral electrode) contact quality monitor, contact quality monitor ground pad socket; a lavage pump system, with a variable speed control, and a control for priming; a processor; a mode indicator, which indicates whether monopolar mode, bipolar mode or APC mode has been selected; a digital display area; and optionally, one or more pull out guides.

Embodiments of the present invention provide a compact electrosurgical apparatus including a generator and a processor, both of which are operably linked to an electrosurgical mode system. The electrosurgical mode system includes a bipolar output system, a monopolar output system, and an argon plasma coagulation (APC) system. The bipolar output system is activated by a bipolar mode selector, wherein the bipolar mode selector allows power to flow from the generator to a bipolar probe socket, wherein the processor controls the flow of power from the generator to the bipolar probe socket, and wherein a bipolar wattage indicator operably linked to the bipolar mode selector displays the amount of power flowing from the generator to the bipolar probe socket.

The monopolar output system is activated by a monopolar mode selector, wherein the monopolar mode selector allows power to flow from the generator to a monopolar probe socket in a desired waveform, wherein the processor controls the flow of power from the generator to the monopolar probe socket and controls the wave form by means of a selectable waveform indicator, and wherein a monopolar wattage indicator operably linked to the monopolar mode selector displays the amount of power flowing from the generator to the monopolar probe socket.

The argon plasma coagulation (APC) output system activated by an APC mode selector, wherein the APC mode selector allows power to flow from the generator to an APC probe socket, wherein the processor controls the flow of power from the generator to the APC probe socket, and wherein an APC wattage indicator operably linked to the APC mode selector displays the amount of power flowing from the generator to the APC probe socket, and wherein the processor controls the flow of argon and indicates a selected flow rate by means of an APC gas flow rate indicator. An argon gas canister is attached to the APC system by means of an argon gas source connector. The APC system also includes an APC gas flow rate adjuster so that the volume of gas can be modified, an APC flow rate indicator that gives a visual cue regarding the gas flow rate, a purge control that allows the operator to purge air or gas in the system, and an argon gas volume indicator that allows the operator to know how much argon is remaining in the canister.

In certain embodiments, the present invention provides a compact electrosurgical apparatus operated by a wireless foot pedal system. The apparatus contains a foot pedal system including a means for transmitting signals, and an electrosurgical system including processor and a means for receiving signals from the foot pedal system.

Other features and advantages of the invention will be apparent from the following detailed description, and from the claims. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. The disclosed materials, methods, and examples are illustrative only and not intended to be limiting. Skilled artisans will appreciate that methods and materials similar or equivalent to those described herein can be used to practice the invention.

DETAILED DESCRIPTION

Monopolar and Bipolar Circuits

Figure 1:
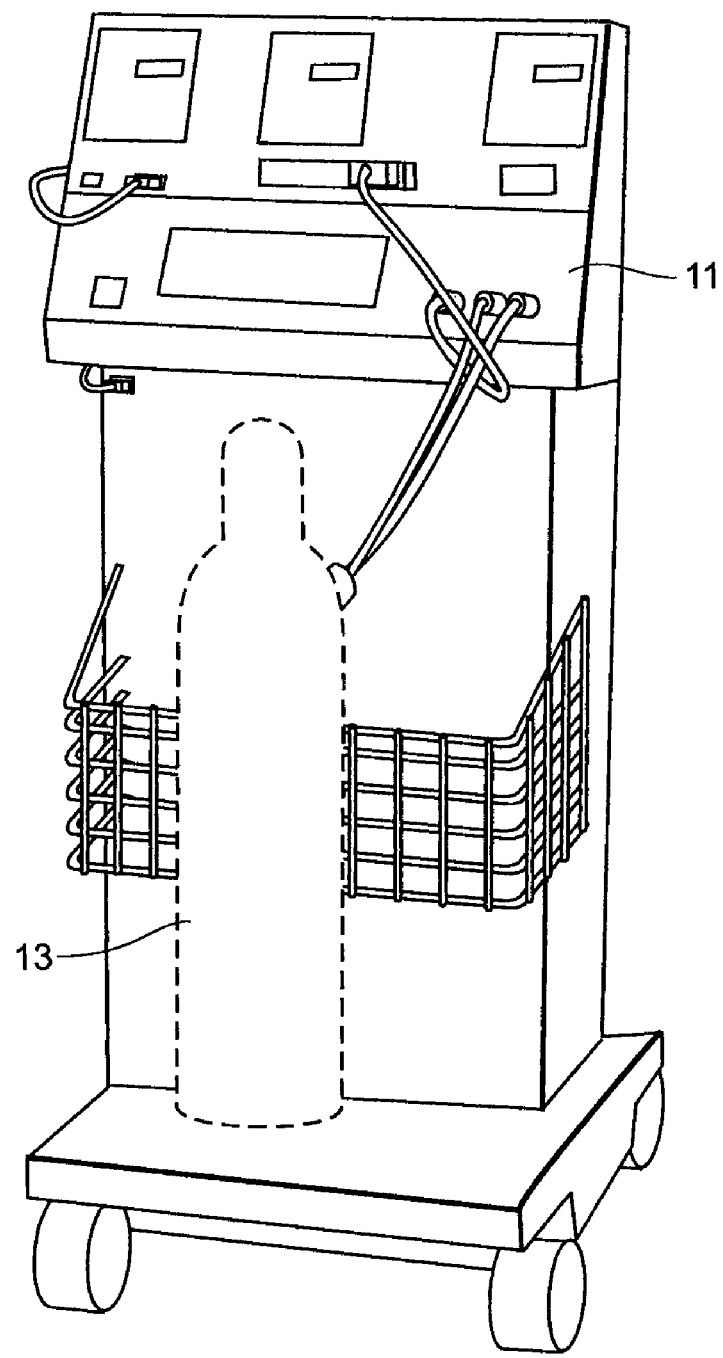
FIG. 1 is a perspective view of a prior art electrosurgical apparatus.

Since electricity requires a complete circuit in order for current to flow, electrosurgical accessories are designed to be either monopolar or bipolar.

With a monopolar accessory, the circuit is completed via a grounding pad. In essence, all of the electrons flow out of the accessory (the active electrode), through the patient, and return to the generator through the grounding pad. In monopolar procedures, correct placement of the grounding pad is important to ensure the best dispersive effect of the energy as it exits the patient.

Bipolar instruments have both the active and return electrodes built into the tip and are thus capable of completing the circuit through the probe without the use of a separate return electrode (grounding pad). The current flows out from the positive pole of the accessory, travels only through a bit of tissue, and is returned by the opposite electrode within the same probe to the generator.

Current Density

Current density is the defining variable in determining specific tissue effects in electrosurgery, yet it is the sum of the effects of several variables.

Current density is the measure of current concentration or, by definition, the current per unit area. The rate of heat generation, and therefore the resulting therapeutic effect, is a function of the current density. It is a measure of intensity. Mathematically, the temperature rises as a square of the current density. Current that will boil water on a square millimeter area will not even feel warm on a square centimeter area. The dramatic difference in surface area between the active electrode and the grounding pad is perhaps the best-understood example of this principle. Current density depends on the applied voltage, current, and type of waveform, as well as the tissue impedance, the size of the electrode and the time that current is flowing.

The effect at the cellular level of the heating caused by sufficiently dense high frequency current varies. The application of high frequency energy intensely to a precise area rapidly heats the tissue to 100° C., causes intracellular water to turn to steam, and causes the cell membrane to explode. This exploding path along an electrode, such as a wire, is what is referred to as "electrosurgical cutting." In biological tissue, voltage peaks must be greater than 200 Vp, and fairly sustained, in order to create current intensity sufficient to create this effect. With less total power applied, or for cells located farther from the electrode, the intracellular water is heated more slowly. At temperatures between 80° C. and 100° C. the water vapor escapes from the cell without bursting the membrane, leaving the cell dry and shrunken with proteins denatured. Electrosurgical coagulation has been the result. The ratio of the total number of cells 'cut' to those 'coagulated' will determine the overall tissue effect.

Of the variables that impact tissue effect, the one that is the most influenced by electrosurgery generator design is that of the high frequency waveform, or output mode. A continuous high frequency waveform with a peak voltage of at least 200 (200 Vp) produces an intensity of current sufficient to create micro electric sparks between the active electrode and the target tissue. Such high current density along the leading edge of the electrode causes cells to literally explode, separating the tissue as if it were cut. As this cell vaporization continues, a micro steam layer is formed which helps to propagate the cutting effect.

Along the edges of the 'cut' there will always be a margin of cells whose distance from the active electrode allows them to heat more slowly. These cells simply coagulate. The depth of this coagulated margin is directly related to the height of the peak voltage in the cutting waveform, and the thickness of the electrode. Higher voltages leave a thicker margin of coagulation, and a thin wire leaves less coagulation than a flat blade.

Even with a continuous waveform, if the voltage never goes above 200 Vp, no cutting can occur. Such outputs lack the intensity to initiate the initial sparking necessary to produce the cutting effect. Instead, a superficial coagulation results. To produce a deeper tissue effect with a lesser degree of electrosurgical cutting and an increasingly greater proportion of coagulated cells, the continuous waveform is interrupted or modulated. Interrupting the waveform delivers energy more slowly, even at the equivalent power settings. To increase the depth of the coagulation the voltage spikes are increased. This is necessary because along the coagulating margins of the electrode path, the impedance is rising as the tissue is coagulated. The thin desiccated layer of coagulation produced by low voltage continuous waveforms do not limit the penetration of these high voltage spikes which force the current through the desiccated layer, increasing the depth of the coagulation. Varying the degree of modulation and the voltage peaks allows the designers of electrosurgical generators to create output modes that hope to predict a predominate tissue effect.

The next two variables that can be moderated to change tissue effect are the power setting and the time the current flows. They are intimately related since energy per unit of time is power measured in watts, and time multiplied by power equals total joules of heat produced. Time has the distinction of being the only electrosurgical variable that is completely controlled by the operator.

The final temperature (T) of the target tissue is defined by the equation: $\Delta T = J^2 pt/CD$, where t=time of current flow and CD is tissue density and its specific heat. Given the same amount of tissue, the same temperature can be achieved by selecting a high power and a short time or a lower power with a longer time. In either case, the same total amount of energy may be delivered but the electrosurgical effect can be radically different. Imagine the difference in clinical effect between using a snare to deliver power set at 50 watts for 2 seconds, or 20 watts for 5 seconds. The total joules of energy would be equal (100 joules) but the tissue effect would not. Another observation is that less tissue destruction occurs if the same total energy is delivered in short bursts rather than continuously. The pauses give the underlying tissue a chance to dissipate the heat.

The heat equation above can be related to the change in tissue effect with a change in waveform by the equation:

$$V \times C = P, \text{ where } V = \text{voltage}, C = \text{current}, \text{ and } P = \text{power in watts.}$$

If both the time and the power setting are kept constant, either a continuous (cut) or modulated (coag) waveform will deliver the same total energy. The tissue effect however, will change from one with little hemostasis and copious cutting to one with deep hemostasis and little electrosurgical cutting.

The physical law that relates all of the electrosurgical variables has been elegantly summarized by Ohm in the equation $P = I^2 R$. The $P = V \times C$ derivation of this equation has already been discussed in relating the type of waveform to total power. Ohm's Law defines another principle crucial to a clinical understanding of electrosurgery: as impedance in tissue rises, power (either current or voltage) decreases. The narrow power curve, ideal for bipolar probes is an excellent example of this fundamental principal.

The narrow power curve works well to produce superficial coagulation with either a monopolar or a bipolar contact electrode. It is not ideal for procedures such as snare polypectomy, where maintaining adequate power to sustain at least some electrosurgical cutting along with deeper coagulation is needed. In order to keep power constant in the face of rising impedance, either voltage or current must be increased.

Argon Plasma Coagulation

Most materials are insulators in that the electrons are so tightly bound in the individual atoms that they do not permit a flow of electron charge. However, if an electric field acting on the material is high enough, the most loosely bound electrons are torn from their atoms allowing current flow. This process is called ionization. Different materials ionize more or less easily. Argon gas is one material that becomes conductive (ionized) quite easily. In its ionized state it is called, like all ionized gases, a "plasma."

The first clinical applications of ionization were developed for use in open surgery procedures. Argon proved ideal not only because it is ionized at relatively low voltages, but it also forms a stable plasma phase, is chemically inert and inexpensive.

The basic mechanism of argon plasma coagulation (APC) is the conduction of high frequency thermal energy to target tissue via the now fluid electrons in the plasma arc. Indications for its use are producing coagulation for hemostasis or tissue devitalization. APC has many desirable characteristics that differentiate it from classic contact desiccation. These include a non-contact route that adds speed and convenience especially when treating large or diffuse lesions. The arc is not unidirectional but instead follows the electric field to tissue seeking to complete the monopolar circuit. APC produces a fairly superficial eschar that is thinner, more flexible, and adherent than those produced with conventional means. The eschar is therefore less likely to re-bleed.

An APC system will include a gas source with control and a specialized electrosurgery generator to provide the voltage source. The actual ionization of the argon takes place when a slightly recessed electrode at the distal tip of the probe accessory activates gas flowing through the flexible probe lumen. The physician has control of the distance the probe tip is held from the tissue, the flow rate of the gas, the power setting on the generator, and the time of application.

The length of the plasma arc between the probe tip and tissue is directly related to the power setting and the resistance of the target tissue, and to a lesser extent, the flow rate of argon. While the design and advantages of APC systems are to provide a non-contact modality, the arc distance in vivo is usually only about 2 to 5 mm. It is clearly unsafe to embed the probe tip into the tissue while it is being activated. Only the gas that has been ionized conveys the thermal effect to tissue. Excess argon outside the ionized arc zone has no thermal effect. Since higher flow rates of gas add little to the tissue effect, but more to patient discomfort due to extra distension, flow rates are commonly set at less than 2.0 L/m.

Overall, power settings between 20 and 90 are most commonly reported. In general, watts of 20 to 60 are used to produce hemostasis of superficial vascular lesions, and watts of 40 to 90 for tissue ablation. Power setting averages differ with APC generator models. As in all electrosurgery, time of application emerges as a critical physician controlled variable.

In summary, physicians control the electrosurgical effect through their choice of electrode, power setting, output mode and application time. The tissue surrounding the active electrode is heated to a depth dependent upon the current density and the time current is allowed to flow.

Desiccation/Broad Hemostasis:

Desiccation or broad hemostasis results from direct contact application of the active electrode with the target tissue. This is accomplished with either mono or bipolar circuit. It is most effectively achieved with broad electrodes, such as biopsy forceps, bipolar probes, or ball tip electrodes. The operator will use the lowest possible power and voltage settings so as to minimize unwanted sticking and sparking. The time of application will greatly affect depth of tissue injury. Rapid, broad non-contact hemostasis is achieved with argon plasma coagulation.

Fulguration:

Fulguration is the non-contact application of a high voltage current without the assist of argon. The distinction between a "coag" waveform that produces desiccation and one that produces fulguration is a matter of the height of the voltage peaks and whether or not the electrode is in direct contact with tissue. High voltages are required to induce current to arc through highly resistant, plain air. Because of unpredictable direction and depth of penetration caused by these intense, high voltage sparks, true non-contact fulguration is rarely used in flexible endoscopy.

Coaption:

Coaption is the concept of applying both pressure and current to seal a vessel. Coaption is most easily achieved with a bipolar probe and low voltage bipolar output, or a ball tip electrode with the lowest available voltage monopolar setting.

Ablation:

Ablation is used to destroy and eliminate surface tissue. It is most effective with a broad contact electrode with a "blended" or "coag" output with a duty cycle of at least 6% to allow for some cutting and marked hemostasis. Argon plasma coagulation may also be used to effectively ablate tissue.

Cutting:

For a cutting effect with minimal hemostasis, the thinnest wire electrodes are chosen with the lowest voltage cut waveform. "Cut" waveforms with increasing voltage will increase the depth of the margin of hemostasis. Selecting a broader wire or moving the wire more slowly will also increase hemostasis, as will choosing a waveform with some modulation. Modulated waveforms with duty cycles between 50 and 100% are common for cutting with hemostasis (coagulation). Coagulation increases as the duty cycle decreases.

Instrument Components

The embodiments of the invention house in one compact unit an electrosurgery generator (which can be used in either monopolar, bipolar or APC mode), an argon plasma coagulation (APC) unit with argon gas provided by a novel, compact disposable canister, and, optionally, a variable speed lavage pump designed to use disposable tubing products. In one embodiment the lavage pump system is a standalone unit that may be non-permanently coupled to the apparatus via a communicating plug in device. The electrosurgery apparatus incorporates abundant features for safety and convenience including a stand-by mode, handy active cord manager, and, in some embodiments, a wireless remote footpedal operation (a footpedal connection cable is also provided for optional use). The apparatus is operated by a compact foot pedal with stand-by engage/disengage switch, for power and water activation pedals. It is important that the present apparatus is a small, compact unit that can easily fit onto a flexible endoscope cart or on small carts/shelves currently used in the medical profession. The compact electrosurgical apparatus of the embodiments of the present invention can be used in a wide variety of medical applications including, without limitation, gastroenterology, bronchoscopy, gynecology, urology, and cardiology.

The compact electrosurgical apparatus of the present invention is less than about 15 inches tall, about 12 to 20 inches wide, and about 12 to 20 inches deep. In one embodiment, it is about 11 inches tall, about 16 inches wide and about 16 inches deep. Also, because the embodiments of the compact electrosurgical apparatus of the present invention use a novel gas container that is housed within the unit itself and that is much smaller than those currently used, the weight of the apparatus in combination with the gas canister can be as much as 100 pounds lighter, and thus much more readily moved by medical personnel.

A. Bipolar Output System

The present apparatus includes a bipolar output system, which includes a bipolar mode selector, a bipolar probe socket, and a bipolar wattage indicator. In certain embodiments, the bipolar mode indicator can be pre-set to a default start point setting. The bipolar output range is from about 2 to 50 watts adjustable in 1 watt increments. In certain embodiments, the apparatus accepts any standard gastroenterology bipolar endostasis probe. The bipolar probe is plugged into the bipolar probe socket. Bipolar probes include a flexible tube enclosing a positive pole and a negative pole, and a fluid connection, such as a lumen for washing when attached to water output from the integrated lavage pump. In certain embodiments, the bipolar wattage indicator is a gauge, a digital screen, or other visual indicator.

In certain embodiments, the bipolar output is a constant less than 200 volt peak (e.g., 190 volt peak) 100% duty cycle wave with a power/impedance curve that conforms to "Tucker's ideal output" for use with bipolar endoscopic hemostasis probes. The unit is compatible with any manufacturer of these probes. When used with an output with this ideal power/impedance curve, bipolar endostasis probes produce high current and power at low impedances (frank blood) with power and current quickly diminishing as tissue is coagulated and the impedance approaches about 100 to 500 ohms. This output power curve enhances the self limiting effect inherent to the performance of the probe.

B. Monopolar Output System

In certain embodiments, the apparatus includes an adjustable monopolar output system. The monopolar output system includes a monopolar mode selector, a monopolar active cord/probe socket, a set of waveform selection indicators each with the ability to be pre-set at chosen start point default watt settings, and a monopolar wattage indicator. The apparatus may further include a monopolar probe operably linked to the apparatus by means of the monopolar active cord/probe socket, wherein the monopolar probe is a snare accessory, a knife accessory, a monopolar ball tip fulgerator, hot biopsy forceps, or other device designed for therapeutic use. In certain embodiments, the monopolar wattage indicator is a gauge, a digital screen, or other visual indicator. In certain embodiments, the waveform indicator includes a series of buttons, a rotatable dial, a movable lever, a touch-sensitive computer screen, or any other mechanism that allows for alternative waveform selection.

In certain embodiments "soft coag" is a 100% duty cycle, 190 Vp constant voltage waveform with a narrow power/impedance curve which will typically produce self limited gentle tissue electrocoagulation with no ability to produce electrosurgical cutting. "Coag" is a modulated 6% duty cycle, moderately high crest factor waveform, designed to produce some electrosurgical cutting when concentrated along a thin electrode, such as a polypectomy snare wire, with concurrent production of significant coagulation. In certain embodiments "coag blend" is a modulated 18% duty cycle, waveform with crest factor below the "coag" mode intended to produce significant coagulation but with increased cutting. In certain embodiments "blend cut" is a modulated 50% duty cycle waveform designed to produce a balance of cells cut and coagulated in most tissue types. In certain embodiments "pulse cut" is a continuous 100% duty cycle 1.4 crest factor wave form with peak voltage constant at less than 500 Vp designed to produce nearly all cutting effects and interrupted at intervals of about every 600- to 700 milliseconds to provide controlled incremental cutting. In certain embodiments "cut" is a continuous 100% duty cycle 1.4 crest factor wave form with peak voltage constant at less than 500 Vp designed to produce nearly all cutting effects.

In certain embodiments, the selected waveform watt output can be inhibited with a stand-by option (0 watts) for additional safety. Pre-set start point watt selections can be made from the following ranges all in one watt increments: soft coag (2 to 120 watts, such as about 60 watts), coag (2 to 120 watts, such as about 25 watts), coag blend (2 to 200 watts, such as about 25 watts), blend cut (2 to 200 watts, such as about 50 watts), pulse cut (2 to 200 watts, such as about 60 watts), and cut (2 to 200 watts, such as about 60 watts). Wattage can be varied by increasing or decreasing the wattage from these pre-set points.

Highly modulated waveforms are typical for snare polypectomy and endoscopic mucosal resection (EMR), and in certain embodiments, the present apparatus provides these types: a 6% duty cycle "Coag", an 18% "Coag Blend" and a 50% "Blend Cut." In certain embodiments of sphincterotomy, a 250 maximum watt controlled voltage 100% duty cycle with an interrupted "pulse cut" mode is offered, as this type of output is proving to be the desired output for limiting "zipper cuts". A standard 100% duty cycle controlled voltage "cut" mode is included. All modes may be pre-set to default start point watts. A 190 constant voltage continuous sine "soft coag" setting may also be pre-set, for use used with ball tip fulgerators. A high voltage (>5000 Vp) wave adequate to produce consistent ionization for APC may also be pre-set. Default start point settings are helpful for users and provide an automatic safety guideline. Wattage can be varied by increasing or decreasing the wattage from these pre-set points.

In certain embodiments, the compact electrosurgical apparatus has contact quality monitoring (CQM) for use with any standard split grounding pad for safety during monopolar procedures including APC. The unit uses processor control to monitor tissue impedance and adjust power output on demand in monopolar contact modes. These features are accepted in the industry as the highest level of safety and performance and yet have not routinely been available in compact electrosurgery units targeted to specialty markets. Isolated, balanced output is a minimum safety standard. Split pads with Contact Quality Monitoring (CQM) help prevent grounding pad burns. Processor control for power on demand helps keep performance smooth and predictable. In certain embodiments, all monopolar modes the CQM indicator lights are red for split pads absent or detecting impedances outside of the assigned ranges and green for pad impedance in the acceptable range, and yellow for single pad in use. In certain embodiments, an audible alarm sounds if the CQM detects impedances at the grounding pad outside of acceptable ranges anytime during the monopolar activation. The CQM indicator lights remain unlit when bipolar mode or pump alone modes are chosen. The CQM system monitors all monopolar functions including APC.

The apparatus has monopolar outputs that have been shown to be safe and clinically effective for snare polypectomy, snare endoscopic mucosal resection (EMR), knife or wire sphincterotomy (with cut or a pulse cut mode), monopolar ball tip fulgerators, hot biopsy forceps, and APC probes. Appropriate wattage settings can automatically default as start points with each output mode selected. The unit can also incorporate a simple programming sequence feature to save end user preferences.

C. Generator

The present apparatus includes a generator, which is a voltage and high frequency alternating current source for the apparatus. The generator provides power for one or more of the following systems: the bipolar output system, the monopolar output system, the APC system, and the lavage pump system. The generator produces alternating currents in frequency ranges greater than 200,000 Hz (hertz) but less than 600,000 Hz.

In certain embodiments, such as where an APC system is present, the APC system is activated by the same power pedal as other functions. APC can also be pre-set at any start point between the watt range of about 10 to 100 watts.

D. Argon Plasma Coagulation (APC) System

In certain embodiments, the apparatus includes an argon plasma coagulation (APC) system. The APC system includes an APC mode selector, an APC probe socket, a gas source connector, an APC flow rate adjuster, an APC flow rate indicator, an APC wattage indicator, and a gas canister volume indicator, and an argon gas purge control. The gas volume indicator provides an indication of the level of gas remaining in the canister. In certain embodiments, the apparatus also includes a grounding pad that is operably linked to the apparatus. In certain embodiments, the apparatus also includes a contact quality monitoring (CQM) indicator that indicates whether the grounding pad is effectively connected to the apparatus and/or effectively in contact with a patient. The CQM may be a visual source (e.g., a light) or audible source (e.g., a mechanism that makes an audible sound) or both if the grounding pad is not appropriately positioned on the patient, indicating impedance measures in an acceptable range (ranges meet international standards) or if the grounding pad is not securely connected to the apparatus.

In certain embodiments, the apparatus recognizes any standard single or split grounding pad, however the full CQM safety system is only engaged with dual or split pads. The apparatus constantly monitors the pad surface for adequate contact area for safety meeting current standards. In one embodiment, the CQM indicator is a light system using the following signals:

Light off for bipolar selection;
Light yellow when a single pad is engaged;
Red light when no pad is engaged and Monopolar or APC modes are selected; or an out of range impedance is detected with a dual pad and monopolar modes
Green when dual pad is both plugged into the system, registers safe contact with a patient, and Monopolar or APC modes are selected.

In certain embodiments, and audible signaling system can be used in addition to the visual system. For example, No sound for bipolar selection;
No sound when a single pad is engaged; but an audible alarm if safe impedance ranges are exceeded during operation with a single pad
Steady "beep" when no pad is engaged and Monopolar or APC modes are selected;
One "beep" when dual pad is both plugged into the system, registers safe contact with a patient, and Monopolar or APC modes are selected.
Audible safety alarm tones if impedance measures at the pad site indicate an unsafe range with either split or single pads.

CQM is a widely recognized safety feature and this signaling system takes into account customer feedback concerning a desire for a system that is easy to understand and subtly alerts that a grounding pad is not needed with bipolar applications.

In certain embodiments, the gas volume indicator is an indicator that is activated when gas decreases to a predetermined volume, such as a gauge that provides a visual indication of the remaining volume of gas in the canister; or a system of indicator lights. The gas volume indicator may be a visual source or audible source.

In certain embodiments, the apparatus includes a gas canister operably connected to the gas source connector. In certain embodiments, the canister is a compact argon gas source which is a disposable, compact canister and has a volume of 2 to 10 liters of compressed 99.9% pure medical grade argon. A unique advance that enables the present apparatus to achieve the market's desire for a truly compact APC system is the novel use of a small disposable canister for the argon gas. The canister easily attaches to the compact electrosurgical apparatus. In one embodiment, the canister simply screws into a specially designed port located within the housing of the apparatus with a convenient access door on the compact electrosurgical apparatus. For example, a pierce top connects the canister to a pressure regulator permanently housed within the unit. A pressure release valve inside the door allows for safe canister changes. The need for a canister change may be signaled automatically when a new canister is needed (e.g., by the gas volume indicator, such as a warning light on the front panel that will light when there is still sufficient gas to complete an average procedure). In certain embodiments, the canister is easy to insert and provides enough gas for 2 to 10 average procedures. A compact, disposable argon canister is important to the design of a small unit to meet this market need.

In certain embodiments, the APC flow rate adjuster allows a gas flow rate of between about 0.2 and 3.0 L/min. Current research indicates that the most desirable flow rate for GI procedures is about 1.0 L/min. For bronchoscopic applications, flow rates between about 0.3 and 0.5 L/min are common. In certain embodiments, the flow rate adjuster is a dial, a push key; a digital output mechanism, a lever, or any other means for an adjusting the gas flow rate.

The apparatus requires the use of a disposable or reusable APC probe operably linked to the APC probe socket, wherein in some embodiments the APC probe consists of a flexible hollow tube, having a proximal end and distal end, and an ionizing electrode positioned at the distal end of the probe tip. In certain embodiments the present apparatus can use back flow filtered APC probes or APC probes that require a separate back flow filter using standard probe sockets. In certain embodiments the apparatus may use APC probes novel and to be uniquely used with the apparatus via a novel APC probe socket design. In certain embodiments the system can use novel disposable ball tip fulgerators for monopolar non-APC hemostasis and tissue ablation. The system is compatible with any manufacturer's snares (EMR or polypectomy) hot biopsy forceps, sphinctertomes, and bipolar endostasis probes, as well as those manufacturer's active cords, which are various therapeutic accessories required for procedures done in endoscopy. In certain embodiments, the active cord is neatly stored when not in use.

E. Lavage Pump System

In certain embodiments, the apparatus also includes a lavage pump system. The lavage pump system includes an attachment for tubing with an inlet port, and outlet port, a rate control adjuster, and a pump. The rate control adjuster includes a series of buttons, a rotatable dial, a movable lever, a touch-sensitive computer screen, or any other mechanism that allows for changing the rate of flow through the tubing attached to the lavage pump. In certain embodiments, the lavage pump further includes a means for preventing backflow. In certain embodiments there is pump speed limit engaged when the bipolar mode is selected. Certain embodiments also include a bottle holder affixed to the apparatus to hold the lavage solution (e.g., sterile water) bottle, and/or a lavage pump bracket to hold any tubing that runs from the solution bottle to the lavage pump.

A lavage pump provides the necessary water source for bipolar probes, and serves for all lavage functions. Flexible endoscope manufacturers increasingly incorporate internal desirable channels for washing. When attached to the generator apparatus, with the electronic interface mechanism, the pump on the present apparatus "self limits" (i.e., automatically limits the flow rate) when bipolar is selected, providing added safety. Using disposable tubing and standard sterile water bottles reflect current market best practice. In certain embodiments, the lavage pump uses standard sterile water bottles and a completely disposable tubing system which meets or exceeds all current guidelines for lavage pump safety and cleanliness. Variable speeds make it suitable for multiple lavage applications.

F. Grounding Pad Socket

In certain embodiments, the apparatus includes a grounding pad socket. The cord from the grounding pad is inserted into the socket so as to provide a complete circuit in monopolar applications. In some embodiments this socket may be a standard "Valley Lab" type.

G. Foot Pedal System and Foot Pedal Connector

In certain embodiments, the apparatus further includes a foot pedal system, wherein the foot pedal system has a water-activating mechanism, a standby toggle switch, a power-activating mechanism, and a connecting means, wherein the foot pedal system is operably linked to the foot pedal connector by means of the connecting means. The connecting means may be an electrical cord or a wireless transmitter. In certain embodiments, the foot pedal connector is an outlet, and in other embodiments, the foot pedal connector is an antenna or other wireless receiver.

The foot pedal may be compact, but not too small for operator convenience. It is electronic, water resistant and provides a near-instant response. It may incorporate a toggle switch to activate and deactivate the standby mode. In certain embodiments an additional control on the unit's front panel allows the 'stand-by' mode to be engaged/disengaged by either the foot pedal operator or an assistant using the hand control on the unit. In certain embodiments, different colored pedals and clear labels indicate either water or power. Other systems with non-integrated/communicating pumps require a third, separate pedal for the pump function. Having the standby toggle switch allows the physician or operator to control the safety function of the standby mode.

H. Processor

Figure 5:
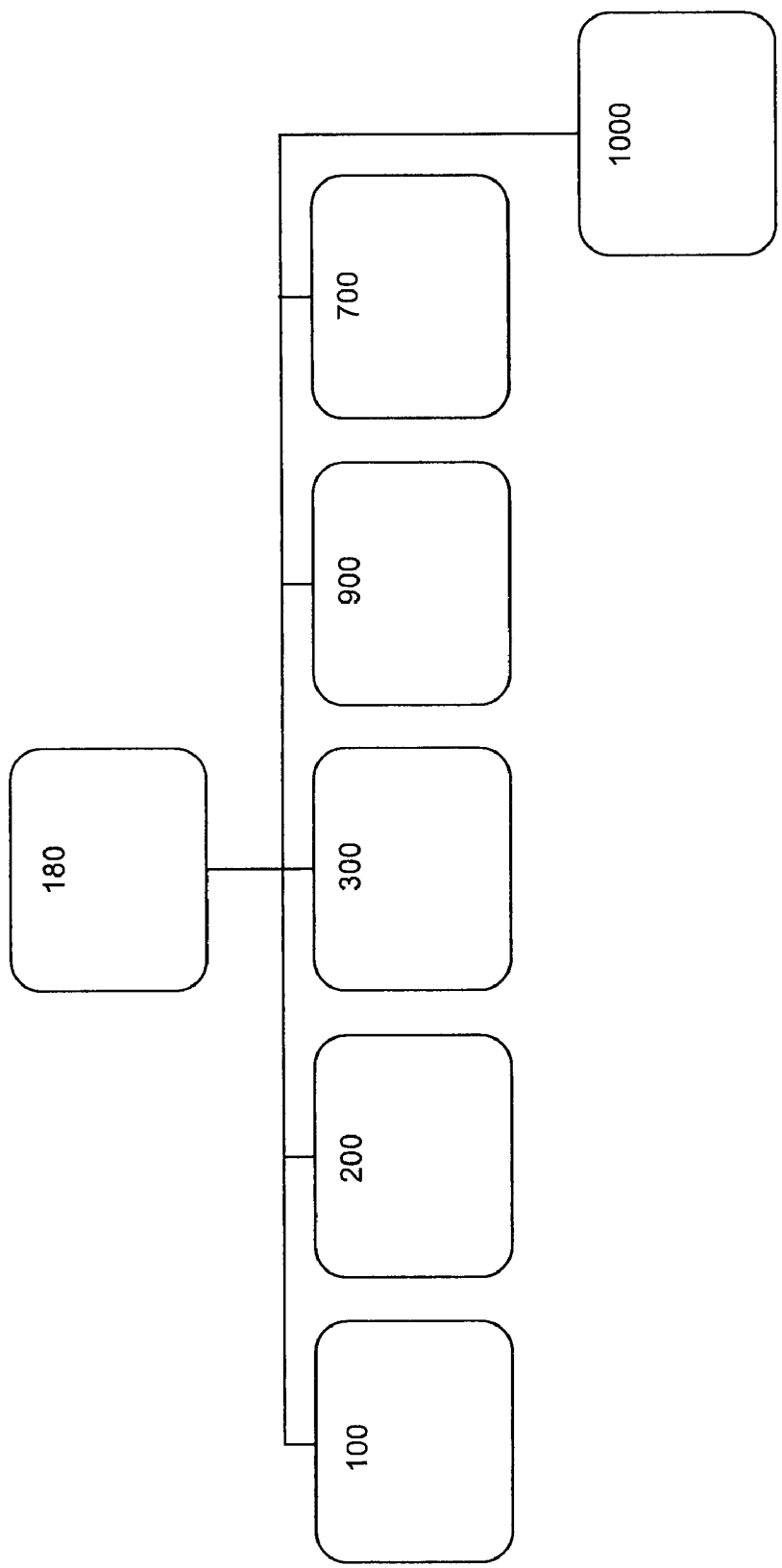
FIG. 5 is a flow chart indicating the interaction of the processor with the bipolar output system, the monopolar output system, the argon plasma coagulation (APC) output system, the foot pedal system, the lavage pump system and the gas canister control system.

The apparatus includes a processor, such as a microprocessor, computer, or other means for sending and receiving electrical signals, and for controlling the electrical elements and processes of the apparatus. A processor regulates power output from the generator based on pre-set or case by case operator-directed levels. The pre-set can be adjusted via a programmable sequence and saved. The processor controls one or more of the bipolar output system, monopolar output system, the APC system, the lavage pump system, the grounding pad socket, the foot pedal system, and the generator, as indicated in FIG. 5. In certain embodiments the processor provides power-up function self-testing, monitors changes in tissue impedance with all contact accessories to regulate power outputs as defined by the power/impedance performance curves, and monitors all safety functions. In certain embodiments, the processor may also include an antenna to transmit and/or receive signals from the foot pedal system.

I. Mode Indicator System

In certain embodiments, the apparatus includes a mode indicator system, which indicates whether monopolar mode, bipolar mode or APC mode has been selected. In certain embodiments, the mode indicator is a series of buttons, a rotatable dial, a movable lever, a touch-sensitive computer screen; digital panel or any other mechanism that allows for alternative mode selection.

J. Pull-Out Guides

In certain embodiments, the apparatus includes one or more pull out guides to indicate suggested monopolar selections or APC settings. In certain embodiments, essential, basic settings and use parameters are featured on simple pull out laminated cards attached to the underside of the unit. This feature incorporates a "tried and true" technology that customers appreciate and that can be considered important for safety. These guides are handy for physicians and nurses to refer to, in order to remind them of approved settings and use parameters. Laminated pull out tabs keep this information handy for quick review, but out of the way and not in patient view. Rarely would the staff have time to enter complicated computer screens to instantly pull up and review this basic information.

K. Exemplary Embodiments

The following is a description of an exemplary embodiment of the compact electrosurgical apparatus of the present invention.

Figure 2:
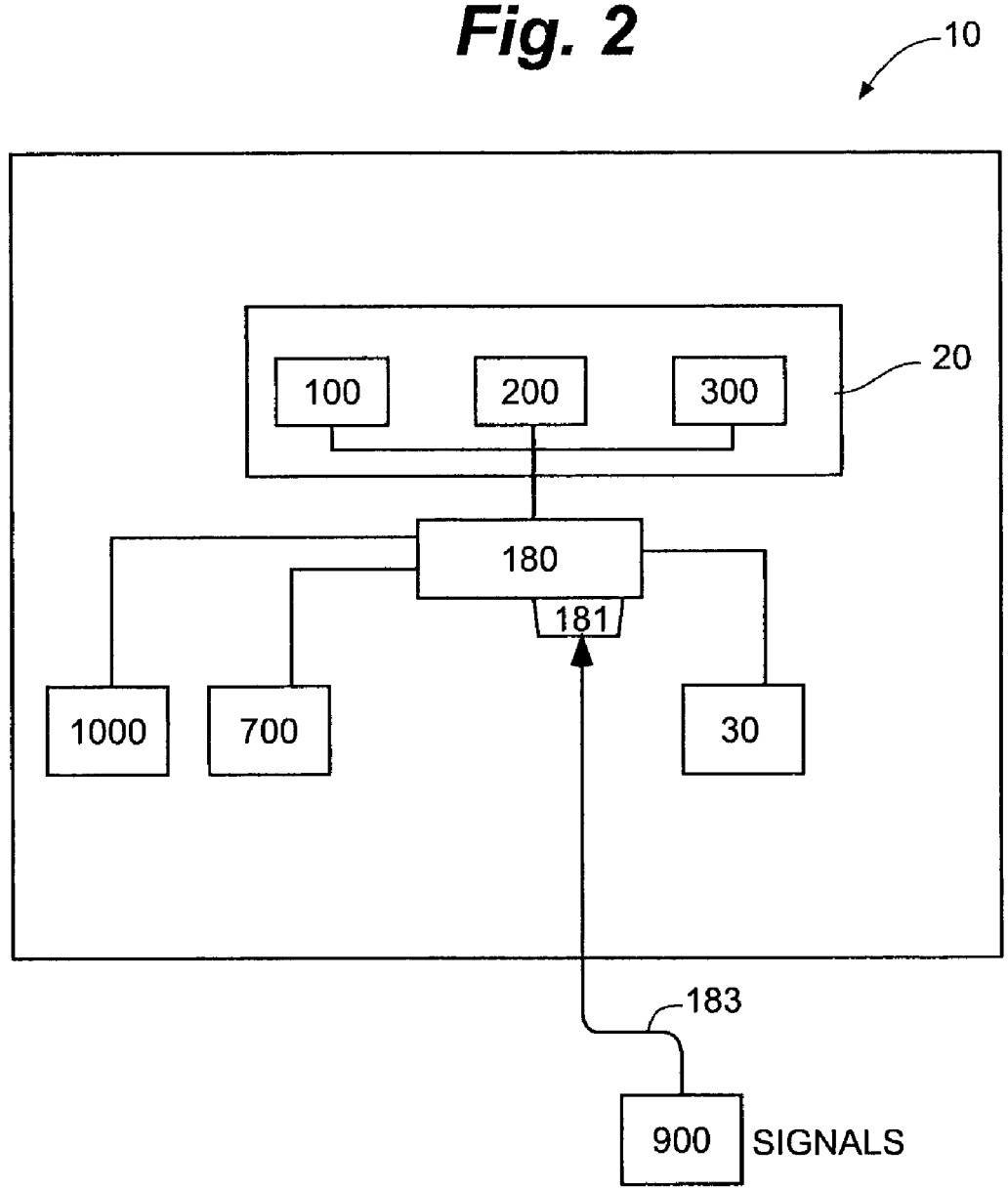
FIG. 2 depicts one embodiment of the electrosurgical apparatus of the present invention.

FIG. 2 depicts one embodiment of the electrosurgical apparatus of the present invention. The apparatus 10 includes an electrosurgical system 20, a lavage pump system 700, and a generator 30, wherein a processor 180 is operably linked to and controls the electrosurgical system 20, the lavage pump system 700, the generator 30 and the gas canister control system 1000, wherein the electrosurgical system includes a bipolar output system 200, a monopolar output system 100, and an argon plasma coagulation (APC) output system 300, and wherein the processor 180 may receive signals from a foot pedal system 900 by means of an antenna 181 or cable.

Figure 3:
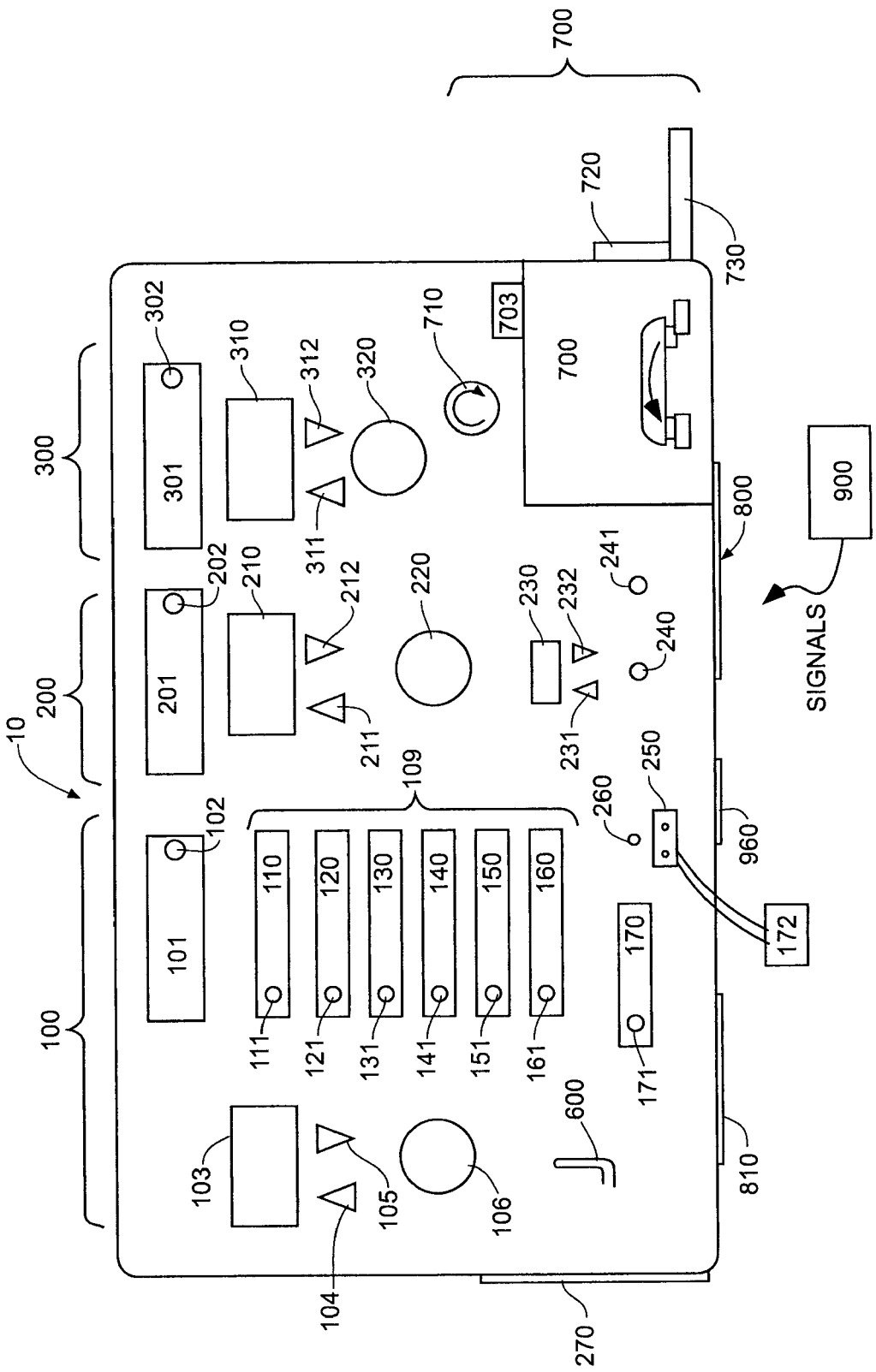
FIG. 3 is a front view of one embodiment of the present apparatus.

FIG. 3 is a front view of one embodiment of the present apparatus 10. The apparatus 10 includes an electrosurgical system 20 a lavage pump system 700, a generator 30 and a gas canister control system (not shown) located in the apparatus, wherein a processor 180 is operably linked to and controls the electrosurgical system 20, the lavage pump system 700, the generator 30 and the gas canister control system wherein the electrosurgical system includes a bipolar output system 300, a monopolar output system 100, and an argon plasma coagulation (APC) output system 200, and wherein the processor 180 receives signals from a foot pedal system 900 by means of an antenna 181 or a cable. The apparatus 10 includes a mode indicator system that includes three indicators: a Monopolar mode selector 101, an APC mode selector 201, and a Bipolar mode selector 301.

This embodiment of the compact electrosurgical apparatus 10 includes a Monopolar output system 100. The Monopolar output system 100 includes a Monopolar mode selector 101, which indicates that the operator has selected to use a Monopolar application. The indicator activates a Monopolar mode indicator light 102 to give a visual cue that this mode has been selected. The Monopolar output system 100 also includes a Monopolar wattage indicator 103 (depicted as a digital screen) that shows the level of wattage output. The operator can raise the wattage level by pressing the Monopolar wattage increase adjuster 104, or lower the wattage level by pressing the Monopolar wattage decrease adjuster 105. In other embodiments, the wattage adjuster can be a dial or other means for varying the wattage output. The apparatus also provides a Monopolar active cord/probe socket 106 into which the operator can insert an active cord to a desired accessory. The present embodiment also provides a Monopolar selectable waveform indicator 109, which is shown in FIG. 1 as set of alternative selectable pre-set waveform indicators, which include the following: Monopolar "soft coag" pre-set waveform indicator 110, Monopolar "coag" pre-set waveform indicator 120, Monopolar "coag blend" pre-set waveform indicator 130, Monopolar "blend" pre-set waveform indicator 140, Monopolar "pulse cut" pre-set waveform indicator 150, Monopolar "cut" pre-set waveform indicator 160, and Monopolar "standby" pre-set waveform indicator 170. The apparatus shows which pre-set indicator was selected by activation of the appropriate indicator light: Monopolar "soft coag" pre-set waveform indicator light 111, Monopolar "coag" pre-set waveform indicator light 121, Monopolar "coag blend" pre-set waveform indicator light 131, Monopolar "blend" pre-set waveform indicator light 141, Monopolar "pulse cut" pre-set waveform indicator light 151, Monopolar "cut" pre-set waveform indicator light 161, and Monopolar "standby" pre-set waveform indicator light 171.

This embodiment of the compact electrosurgical apparatus 10 includes an APC output system 200. The APC output system 200 includes an APC mode selector 201, which indicates that the operator has selected to use an APC application. The indicator activates an APC mode indicator light 202 to give a visual cue that this mode has been selected. The APC output system 200 also includes an APC wattage indicator 210 (depicted as a digital screen) that shows the level of wattage output. The operator can raise the wattage level by pressing the APC wattage increase adjuster 211, or lower the wattage level by pressing the APC wattage decrease adjuster 212. In other embodiments, the wattage adjuster can be a dial or other means for varying the wattage output. The apparatus also provides an APC probe socket 220 into which the operator can insert a desired accessory. The APC output system 200 also includes an APC gas flow rate indicator 230 (depicted as a digital screen) that shows the level of gas flow. The operator can raise the gas flow level by pressing the APC gas flow increase adjuster 231, or lower the gas flow level by pressing the APC gas flow decrease adjuster 232. In other embodiments, the gas flow adjuster can be a dial or other means for varying the gas flow output. The apparatus also provides an APC gas volume indicator 240, which activates when the volume of remaining gas is low. The apparatus also provides a CQM ground pad socket 250, into which the ground pad can be connected to the apparatus. The apparatus also provides a CQM monitor 260, which is activated according to indication system previously mentioned. The apparatus also provides a gas access door 270 which is used to access a gas canister hold and control assembly located inside the apparatus. More particularly, a gas canister, preferably an argon gas canister, is loaded into the gas canister hold which couples it to a control assembly as will be described in further detail with reference to FIG. 10. An argon gas purge control 241 pre-fills an APC probe with an automatically measured amount of argon gas prior to activation.

This embodiment of the compact electrosurgical apparatus 10 includes a bipolar output system 300. The Bipolar output system 300 includes a Bipolar mode selector 301, which indicates that the operator has selected to use a Bipolar application. The indicator activates a Bipolar mode indicator light 302 to give a visual cue that this mode has been selected. The Bipolar output system 300 also includes a Bipolar wattage indicator 310 (depicted as a digital screen) that shows the level of wattage output. The operator can raise the wattage level by pressing the Bipolar wattage increase adjuster 311, or lower the wattage level by pressing the Bipolar wattage decrease adjuster 312. In other embodiments, the wattage adjuster can be a dial or other means for varying the wattage output. The apparatus also provides a Bipolar probe socket 320 into which the operator can insert a desired accessory.

This embodiment of the compact electrosurgical apparatus 10 includes an accessory cord storage bracket 600, which can be used to store cords from an accessory when not in use.

This embodiment of the compact electrosurgical apparatus 10 includes a Lavage pump system 700. The Lavage pump system 700 includes a Lavage pump tubing acceptor mechanism, as is well known to those of ordinary skill in the art. The Lavage pump system 700 also includes a Lavage pump rate control adjuster 710 (depicted as an adjustable dial). This Lavage pump system 700 also includes a Lavage pump bracket 720, which can store tubing used with the Lavage pump system 700, and includes a Lavage pump bottle holder 730 for holding solution bottles. This embodiment of the compact electrosurgical apparatus 10 includes a pullout settings guide 810, and a pull out selection guide 800. These guides are used by operators to assist in determining which settings to use for various procedures. A lavage pump system that may be used with the embodiments of the invention is commercially available from Byrne Medical, Inc. of Conroe, Tex.

Figure 4:
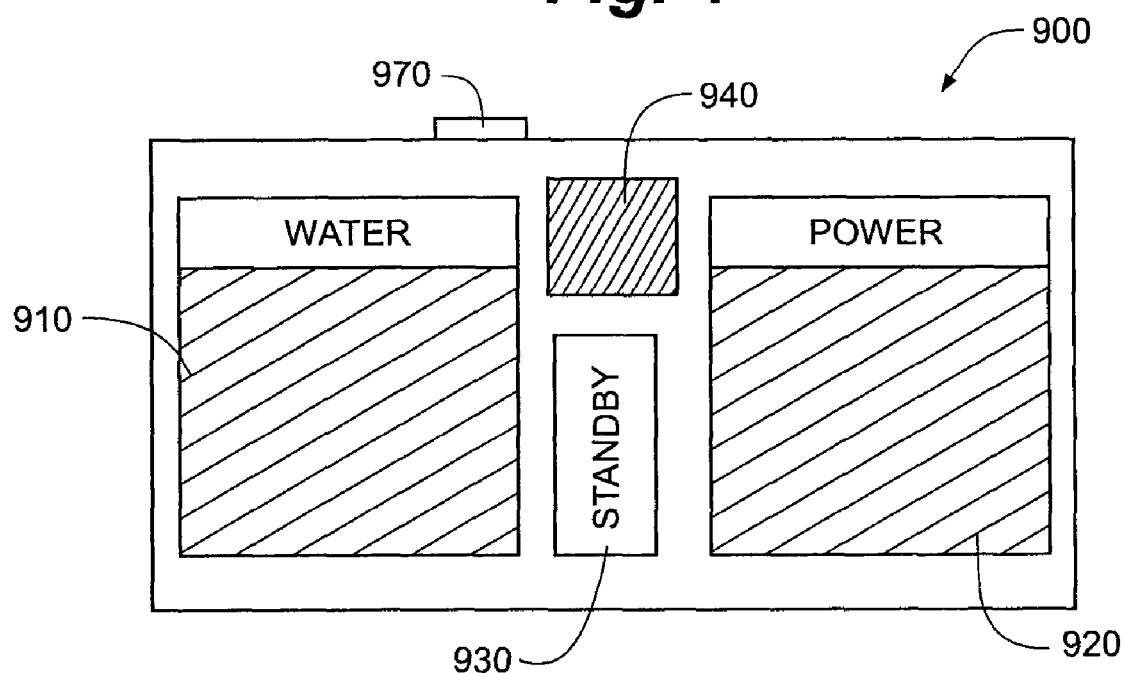
FIG. 4 is a top view of one embodiment of the foot pedal system.

This embodiment of the compact electrosurgical apparatus 10 includes a Foot pedal system 900. FIG. 4 is a top view of one embodiment of the foot pedal system 900. The Foot pedal system 900 includes a Foot pedal fluid activator 910, a Foot pedal power activator 920, and a Foot pedal standby toggle switch 930. In certain embodiments, the Foot pedal system 900 may include a Foot pedal antenna or other wireless transmitter 940 or Foot pedal connector 970 (i.e., a cord). In certain embodiments, the Foot pedal system 900 includes a Foot pedal connector socket 960 into which a Foot pedal connector 970 can be removably plugged.

FIG. 5 is a flow chart indicating the interaction of the processor 180 with the bipolar output system 300, the monopolar output system 100, the argon plasma coagulation (APC) output system 200, the foot pedal system 900 and the lavage pump system 700 and the gas canister control system 1000.

Figure 6:
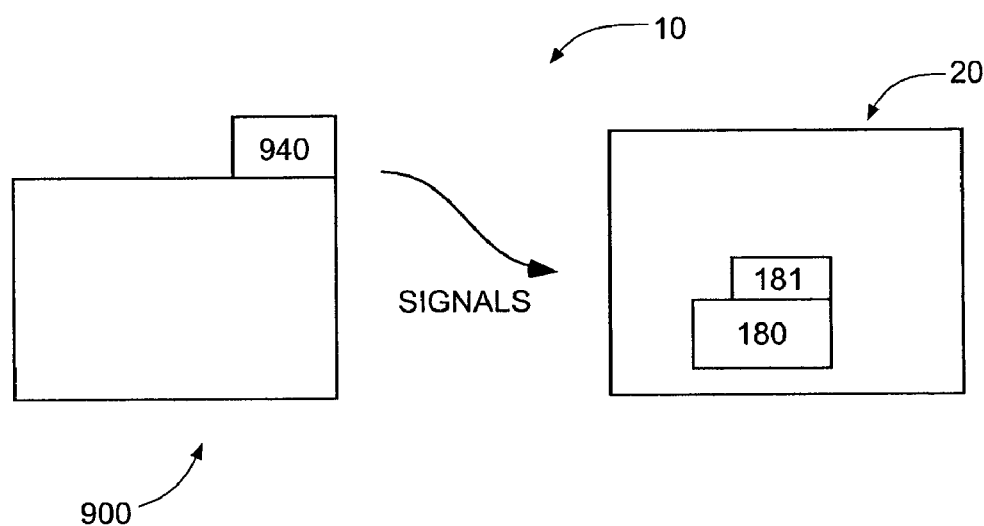
FIG. 6 depicts one embodiment of the apparatus of the present invention.

As shown in FIG. 6, one embodiment of the present invention is a compact electrosurgical apparatus 10. The apparatus 10 includes an electrosurgical system 20, wherein an antenna 181 operably linked to the processor 180 receives signals from a foot pedal system 900 by means of a foot pedal antenna 940. The Foot pedal system 900 includes a foot pedal antenna 940 that transmits signals to the electrosurgical system 20. The electrosurgical system 20 receives the signals by means of an antenna 181, which is operably linked to the processor 180.

Figure 7:
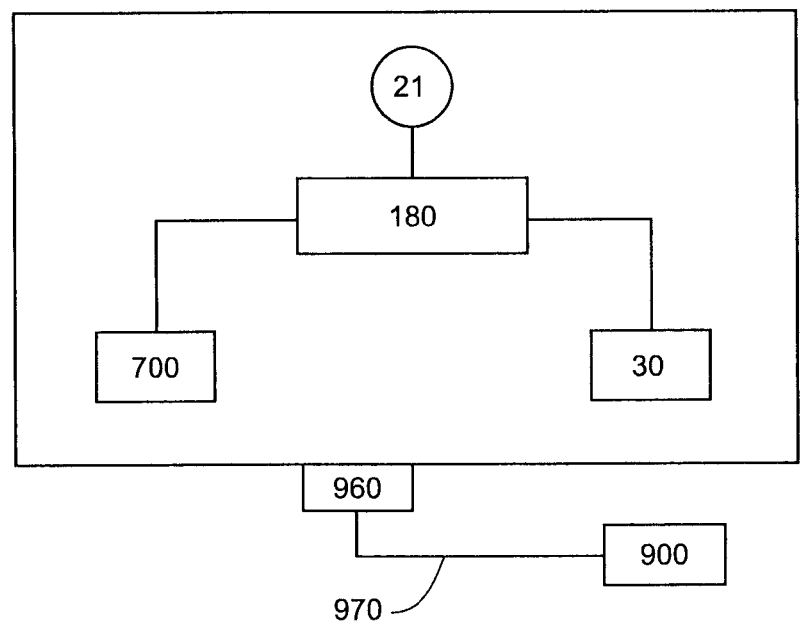
FIG. 7 depicts one embodiment of the apparatus of the present invention.
Figure 8:
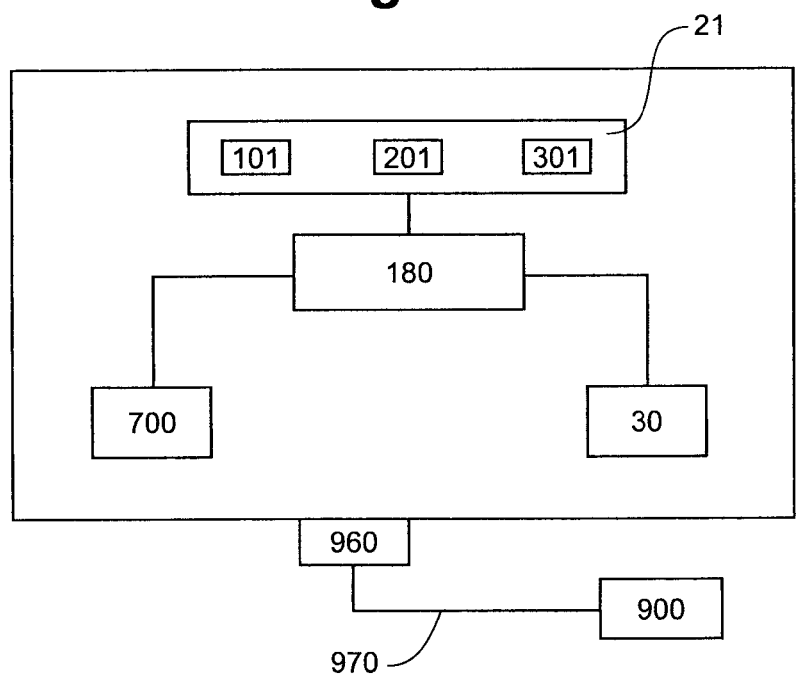
FIG. 8 depicts another embodiment of the apparatus of the present invention.

FIG. 7 depicts one embodiment of the apparatus of the present invention, where the electrosurgical system mode selector is a dial 21. The foot pedal system is coupled to the electrosurgical system by means of a foot pedal connector 970 (e.g. an electrical cord) or wirelessly and the dial 21 is rotated to set positions for selecting monopolar mode, bipolar mode or APC mode. FIG. 8 depicts one, where the electrosurgical system mode selector is a series of toggle buttons 21. The foot pedal system is connected to the electrosurgical system by means of a foot pedal connector 970 (e.g., an electrical cord) or wirelessly, and where the electrosurgical system mode selector is a series of push keys corresponding to the monopolar mode selector 101, the APC mode selector 201, and the Bipolar mode selector 301.

Figure 9:
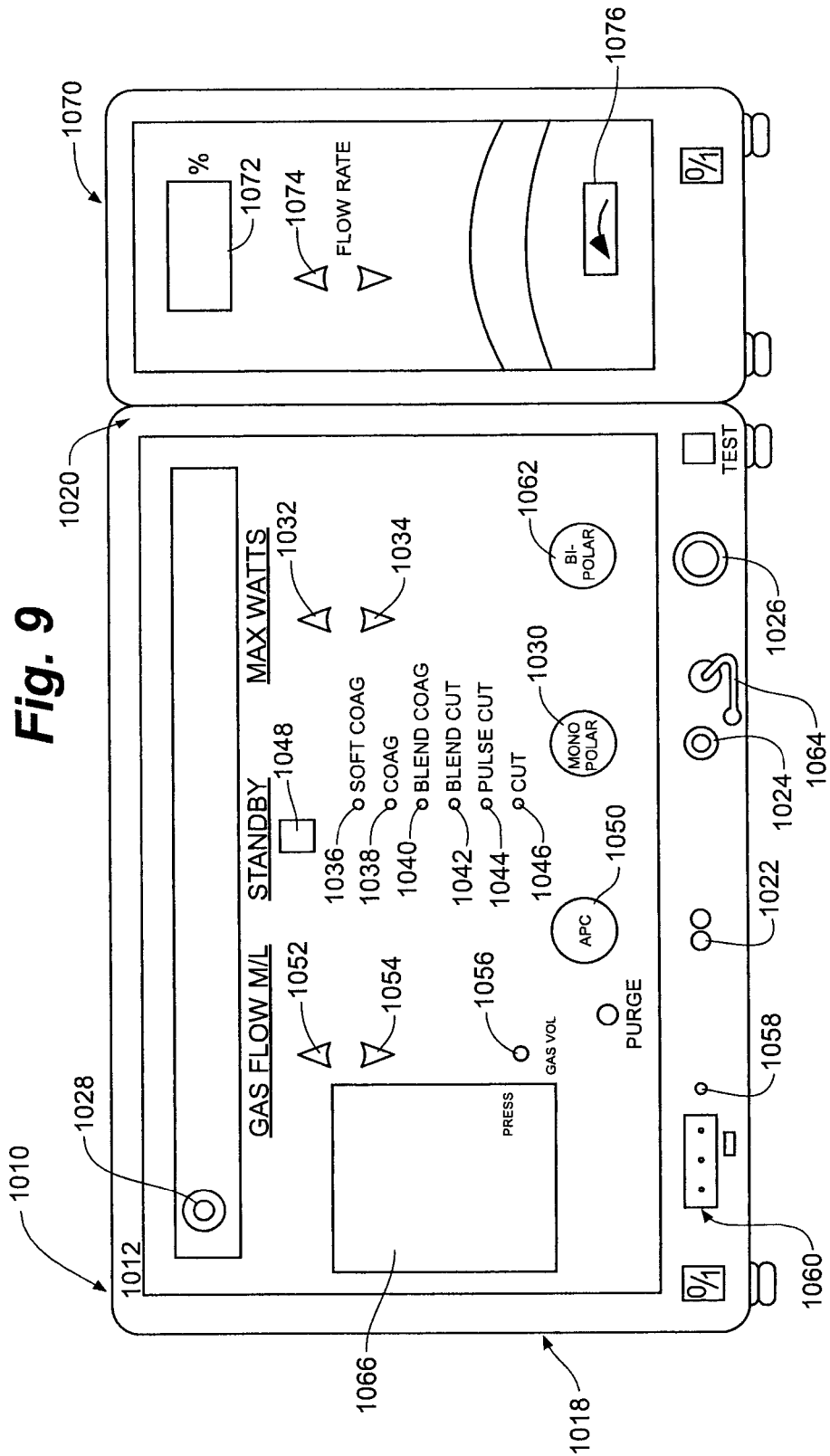
FIG. 9 depicts a front view of an embodiment of a compact electrosurgical apparatus according to the invention.

FIG. 9 depicts a front view of an embodiment of a compact electrosurgical apparatus according to the invention. The compact electrosurgical apparatus includes a housing 1010 that is generally in the shape of a rectangular box and preferably measures about 15 inches (length) by about 10 inches (height) by about 16 inches (depth). The housing includes a front panel 1012, a back panel (not shown) generally parallel with the front panel, a top panel 1014 extending between the front and back panel, a bottom panel 1016 extending between the front and back panel, the bottom panel being generally parallel to the top panel, a left side panel 1018 extending between the front, back, top and bottom panels and a right side panel 1020 extending between the front, back, top and bottom panels, the right side panel being generally parallel to the left side panel. The front, back, top, bottom left and right side panels define a cavity within the housing. Located within the cavity is an electrosurgical system that includes a monopolar output system, a bipolar output system, and an argon plasma coagulation output system such as described above. Also located within the cavity is a processor that is operatively coupled to each output system of the electrosurgical system to control outputs generated by each output system. In addition, a high frequency generator is located within the cavity and is operatively coupled to the processor. Finally an argon gas canister holder and control system is also located within the cavity of the housing for receiving a gas canister within the cavity of the housing and controlling its operation, as will be described in detail hereinafter.

It will be understood by those of ordinary skill in the art, that the layout of the features on the front panel 1012 of the housing may be changed without departing from the scope of the embodiments of the invention. Located along the bottom of the front panel 1012 are a plurality of sockets for receiving accessory devices. In particular, an argon plasma coagulation probe socket 1022 is provided to receiver an argon coagulation probe (not shown) and operatively couple it to the argon plasma coagulation output system. A monopolar probe socket 1024 is provided to receive a monopolar probe (not shown) and operatively couple it to the monopolar output system and a bipolar probe socket 1026 is provided to receive a bipolar probe (not shown) and operatively couple it to the bipolar output system.

The front panel 1012 of the housing displays various parameters. There is a display screen 1028, preferably an LED that displays various parameters to the user depending on the mode the electrosurgical apparatus is operating in.

This embodiment of the compact electrosurgical apparatus includes a Monopolar output system. The Monopolar output system includes a Monopolar mode selector 1030, which indicates that the operator has selected to use a Monopolar application. The selector activates a Monopolar mode indicator display in the display screen to give a visual cue that this mode has been selected. The Monopolar output system also includes a Monopolar wattage indicator (displayed on the display 1028) that shows the level of wattage output. The operator can raise the wattage level by pressing the Monopolar wattage increase adjuster 1032, or lower the wattage level by pressing the Monopolar wattage decrease adjuster 1034. In other embodiments, the wattage adjuster can be a dial or other means for varying the wattage output. The apparatus also provides a Monopolar active cord/probe socket 1024 into which the operator can insert an active cord to a desired accessory. The present embodiment also allows a user to select a particular monopolar waveform by pressing the monopolar mode selector 1030 a prescribed number of times. The apparatus shows which pre-set indicator was selected by activation of the appropriate indicator light: Monopolar "soft coag" pre-set waveform indicator light 1036, Monopolar "coag" pre-set waveform indicator light 1038, Monopolar "coag blend" pre-set waveform indicator light 1040, Monopolar "blend CUT" pre-set waveform indicator light 1042, Monopolar "pulse cut" pre-set waveform indicator light 1044, Monopolar "cut" pre-set waveform indicator light 1046, and Monopolar "standby" pre-set waveform indicator light 1048.

This embodiment of the compact electrosurgical apparatus includes an APC output system. The APC output system includes an APC mode selector 1050 and the display 1028 provides a visual cue that this mode has been selected. The APC output system also includes an APC wattage indicator (displayed on the screen 1028) that shows the level of wattage output. The operator can raise the wattage level by pressing the APC wattage increase adjuster 1032, or lower the wattage level by pressing the APC wattage decrease adjuster 1034. In other embodiments, the wattage adjuster can be a dial or other means for varying the wattage output. The apparatus also provides an APC probe socket 1022 into which the operator can insert a desired accessory. The APC output system also includes an APC gas flow rate indicator (displayed on the screen) that shows the level of gas flow. The operator can raise the gas flow level by pressing the APC gas flow increase adjuster 1052, or lower the gas flow level by pressing the APC gas flow decrease adjuster 1054. In other embodiments, the gas flow adjuster can be a dial or other means for varying the gas flow output. The apparatus also provides an APC gas volume indicator, which activates when the volume of remaining gas in the canister is low and the canister needs to be replaced. The gas volume indicator may be visual or audible. The apparatus also provides a CQM ground pad socket, into which the ground pad can be connected to the apparatus. The apparatus also provides a CQM monitor 1058, which is activated according to indication system previously mentioned and a CQRM grounding pad receptacle 1060.

This embodiment of the compact electrosurgical apparatus includes a bipolar output system. The bipolar output system includes a bipolar mode selector 1062 and the display provides a visual cue that this mode has been selected. The bipolar output system also includes a bipolar wattage indicator (displayed on the screen 1028) that shows the level of wattage output. The operator can raise the wattage level by pressing the bipolar wattage increase adjuster 1032, or lower the wattage level by pressing the bipolar wattage decrease adjuster 1034. In other embodiments, the wattage adjuster can be a dial or other means for varying the wattage output. The apparatus also provides a bipolar probe socket 1026 into which the operator can insert a desired accessory.

This embodiment of the compact electrosurgical apparatus includes an accessory cord storage bracket 1064, which can be used to store cords from an accessory when not in use.

Also located on the front panel is a gas canister access door 1066 which can be accessed by a user to expose a cavity for holding a gas canister located in the cavity of the housing. The door 1066 may be any type known to those of ordinary skill in the art. For example, it can be opened by a user simply pressing the door in a particular location. Located on the front panel next to the gas canister access door is a gas volume indicator 1056 and a gas flow adjuster in the form of up/down switches 1052, 1054. The gas volume indicator 1056 preferably is controlled, as will be explained hereinafter, to activate when the gas canister needs replacement. As previously mentioned the gas volume indicator may be visual such as a light or it may be audible such as a beep. In addition, an output of a gas sensor, as will be described herein after, may send a signal so that a display is made on display screen of how much gas is currently in the gas canister.

Also shown in FIG. 9 is a lavage system 1070 that is shown coupled to the housing of the apparatus. This coupling may be either permanent or temporary. The lavage system 1070 includes a display screen 1072, flow rate control 1074, and a disposable pump tubing cartridge head 1076 as is well know to the of ordinary skill in the art and need not be described in further detail. As previously mentioned such lavage systems are commercially available from Byrne Medical, Inc.

Figure 10:
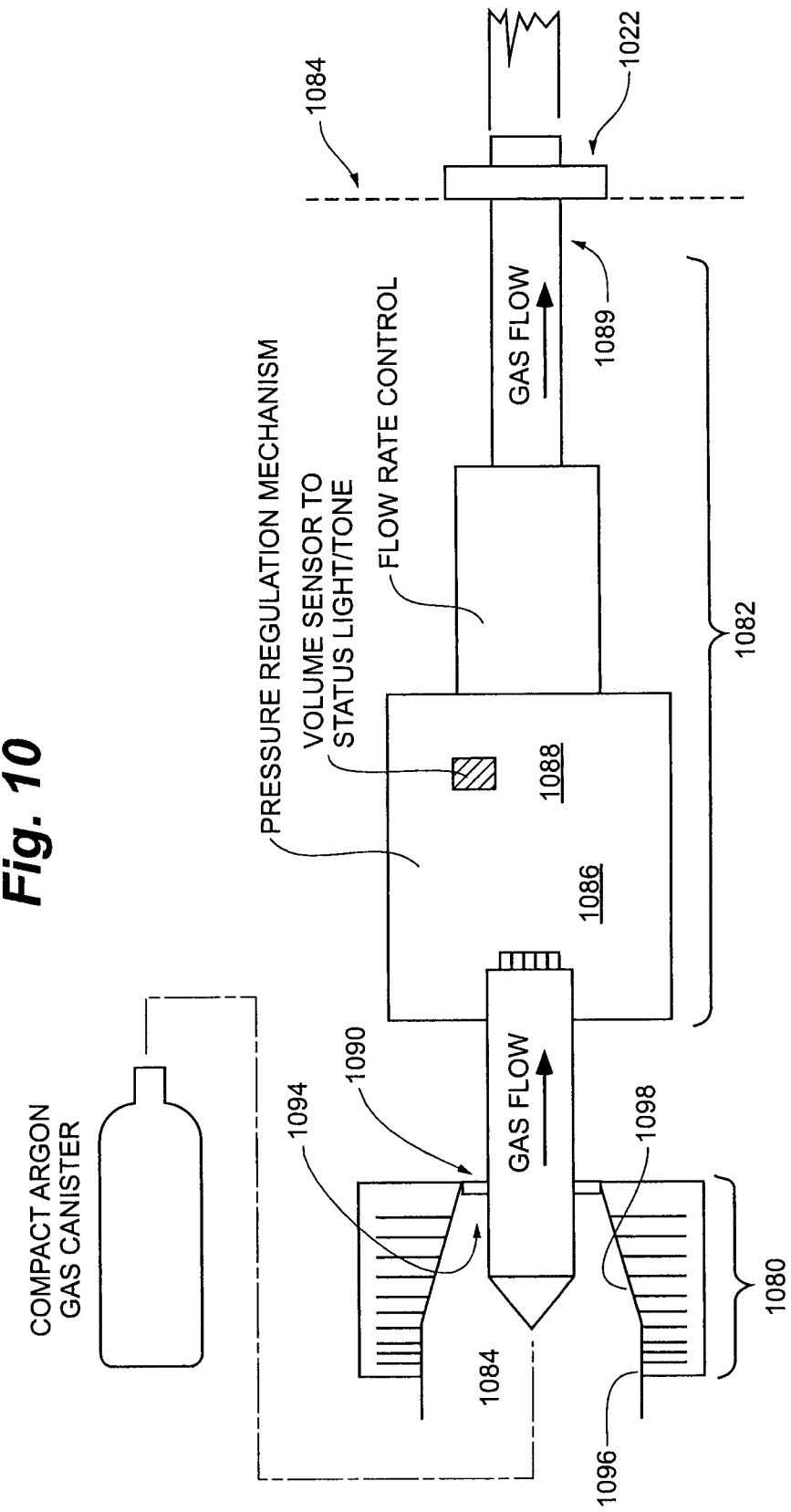
FIG. 10 illustrates a cross-sectional view of the gas canister holder and control system located within the housing shown in FIG. 9.

FIG. 10 illustrates a cross-sectional view of the gas canister holder 1080 and control system 1082 located within the housing shown in FIG. 9. The front panel of the housing is shown at line 1084 Located on the exterior of the front panel of the housing, the term exterior meaning outside the cavity of the housing, is the coagulation probe socket 1022. Located inside the cavity of the housing are a gas canister holder 1080 and control system 1082. The gas canister control system includes a pierce mechanism 1084, a pressure regulator 1086, a gas volume sensor 1088 and gas flow conduit 1089. The pressure regulator 1086 is operatively coupled to the pierce mechanism 1084 and the processor 180. The gas volume sensor 1088 is operatively coupled to the processor 180. The gas flow conduit 1089 is operatively coupled to the front panel of the housing and the pressure regulator 1086. The gas probe socket 1022 located on the front panel of the housing is operatively coupled to the gas flow conduit 1089. The pierce mechanism 1084 may be hollow or solid as is well known. The apparatus also provides a gas source connector with seals 1090, which is used to connect the gas (e.g., argon) canister to the apparatus, and an argon gas purge control (1092, see FIG. 9) that pre-fills an APC probe with an automatically measured amount of argon gas prior to activation.

The gas canister hold 1080 has the pierce mechanism 1084 extending therein and exposed to couple with a gas canister. The hold includes seals 1094 around the pierce mechanism 1084 so that gas does not leak from the canister around the pierce mechanism and escape from the cavity of the housing. The hold has guide walls 1096 to smoothly guide a gas canister into place and screw threads 1098 located on the guide wall adjacent the pierce mechanism for coupling to the exterior of the gas canister. Thus, in use a user simply opens the gas canister door 1066 on the front panel and screws a gas canister into place so that the pierce mechanism pierces the seal of the gas canister and allows gas to flow into the pressure regulator. The pressure regulator receives command signals operatively from the gas flow regulator controls located on the front panel of the housing to control the amount of gas that is delivered to an argon coagulation probe coupled to socket 1022. A volume sensor outputs a signal to the gas volume light on the front panel when the gas canister needs to be replaced. In addition, or alternatively, the gas sensor can send a signal to the display screen on the front panel of the housing indicating that the gas canister needs to be replaced and/or the current volume level in the gas canister.

Various embodiments of the invention have been described. It should be understood, however, that many variations and modifications may be made to these described embodiments while remaining within the scope of the present invention.

What is claimed is:

1. A compact electrosurgical apparatus comprising:
    a housing having a front panel, a back panel generally parallel with the front panel, a top panel extending between the front and back panel, a bottom panel extending between the front and back panel, the bottom panel being generally parallel to the top panel, a left side panel extending between the front, back, top and bottom panels and a right side panel extending between the front, back, top and bottom panels, the right side panel being generally parallel to the left side panel, wherein the front, back, top, bottom left and right side panels define a cavity;
    a high frequency electrosurgical system located within the cavity, the electrosurgical system comprises;
    a high frequency monopolar output system;
    a high frequency bipolar output system;
    an argon plasma coagulation (APC) output system;
    a processor located within the cavity, the processor operatively coupled to each of the output systems of the high frequency electrosurgical system to control outputs generated by each output system;
    a high frequency generator located within the cavity and operatively coupled to the processor; and
    a gas canister holder and a gas canister control system located within the cavity of the housing for receiving a gas canister, wherein the gas canister control system includes
        a pressure regulator operatively coupled to the processor;
        a gas volume sensor operatively coupled to the processor;
        a gas flow conduit operatively coupled to the housing and the pressure regulator; and
        a gas probe socket located on the housing and operatively coupled to the gas flow conduit.

2. The apparatus of claim 1, further comprising a lavage pump system operatively coupled to the processor located in the cavity of the housing.

3. The apparatus of claim 1, further comprising a port located on the housing and operatively coupled to the processor for receiving signals from a foot pedal system coupled to the port wherein the foot pedal system provides a control and signals to the processor.

4. The apparatus of claim 1, wherein the processor generates a gas flow rate control signal to the pressure regulator to control the flow rate of gas from a gas canister coupled to the gas flow conduit.

5. The apparatus of claim 4, further comprising an argon gas purge control operably coupled to the pressure regulator.

6. The apparatus according to claim 4, further comprising a gas volume indicator located on the housing and operatively coupled to the gas volume sensor.

7. The apparatus of claim 6, wherein the gas volume indicator indicates when the gas canister needs to be changed.

8. The apparatus of claim 6, wherein the gas volume indicator indicates the volume of gas remaining in the gas canister.

9. The apparatus of claim 1, further comprising an electrosurgical system mode selector located on the housing and operatively coupled to the bipolar output system, the monopolar output system, and the APC output system, wherein the electrosurgical system mode selector allows a user to select one of the monopolar output system, the bipolar output system, and the APC output system.

10. The apparatus of claim 1 further comprising a bipolar probe socket located on the housing and operatively coupled to the bipolar probe output system wherein the bipolar probe socket may be operatively coupled to a bipolar probe.

11. The apparatus of claim 10, further comprising a bipolar wattage indicator comprising a gauge, digital screen or other visual indication.

12. The apparatus of claim 1, further comprising a monopolar probe socket located on the housing and operatively coupled to the monopolar probe output system wherein the monopolar probe socket may be operatively coupled to a monopolar probe.

13. The apparatus of claim 12, further comprising a monopolar wattage indicator comprising a gauge, digital screen or other visual indication.

14. The apparatus of claim 1, further comprising a selectable waveform indicator operatively coupled to the processor, wherein the selectable waveform indicator is a series of buttons, a rotatable dial, a movable lever, a touch-sensitive computer screen, or any other mechanism that allows for alternative waveform selection.

15. The apparatus of claim 14, wherein the selectable waveform indicator is pre-set with a stand-by option (0 volts) and at least one of the following options: soft coagulation, coagulation, one or more blends, pulse cut, and cut.

16. The apparatus of claim 1, further comprising a port located on the housing and operatively coupled to the processor for receiving a grounding pad.

17. The apparatus of claim 1, wherein the generator provides high frequency alternating power in a bipolar output mode, a monopolar output mode, and an argon plasma coagulation output mode.

* * * * *